US007326531B2

(12) United States Patent
Estell

(10) Patent No.: US 7,326,531 B2
(45) Date of Patent: Feb. 5, 2008

(54) PROTEASES FROM GRAM-POSITIVE ORGANISMS

(75) Inventor: David A. Estell, San Mateo, CA (US)

(73) Assignee: Genencor International, Inc., Palo Alto, CA (US)

( * ) Notice: Subject to any disclaimer, the term of this patent is extended or adjusted under 35 U.S.C. 154(b) by 25 days.

(21) Appl. No.: 11/008,331

(22) Filed: Dec. 8, 2004

(65) Prior Publication Data
US 2005/0244925 A1 Nov. 3, 2005

Related U.S. Application Data

(60) Continuation of application No. 10/328,459, filed on Dec. 23, 2002, now Pat. No. 6,905,868, which is a division of application No. 09/486,192, filed as application No. PCT/US98/18677 on Sep. 8, 1998, now Pat. No. 6,521,440.

(30) Foreign Application Priority Data
Sep. 15, 1997 (GB) ................... 9719637.2

(51) Int. Cl.
C12Q 1/68 (2006.01)
C12N 15/57 (2006.01)
C12N 9/52 (2006.01)
C12N 9/54 (2006.01)
C12N 9/56 (2006.01)

(52) U.S. Cl. .................... 435/6; 435/220; 435/221; 435/222; 536/23.2

(58) Field of Classification Search .................. None
See application file for complete search history.

(56) References Cited

U.S. PATENT DOCUMENTS

| 3,817,837 A | 6/1974 | Rubenstein et al. ...... 195/103.5 |
| 3,850,752 A | 11/1974 | Schuurs et al. ........... 195/103.5 |
| 3,939,350 A | 2/1976 | Kronick et al. ............. 250/365 |
| 3,996,345 A | 12/1976 | Ullman et al. ................. 424/12 |
| 4,261,868 A | 4/1981 | Hora et al. .................. 252/529 |
| 4,275,149 A | 6/1981 | Litman et al. .................. 435/7 |
| 4,277,437 A | 7/1981 | Maggio ........................ 422/61 |
| 4,366,241 A | 12/1982 | Tom et al. ...................... 435/7 |

(Continued)

FOREIGN PATENT DOCUMENTS

DE 21634 4/1982

(Continued)

OTHER PUBLICATIONS

EMBL/GENBANK Accession No. BSUB0006, Kunst et al., Apr. 18, 2005.*

(Continued)

Primary Examiner—Nashaat T. Nashed
Assistant Examiner—William W. Moore

(57) ABSTRACT

The present invention relates to the identification of novel metallo-proteases (MP) in Gram-positive microorganisms. The present invention provides the nucleic acid and amino acid sequences for Bacillus MP. The present invention also provides host cells having a mutation or deletion of part or all of the gene encoding MP. The present invention also provides host cells further comprising nucleic acid encoding desired heterologous proteins such as enzymes. The present invention also provides cleaning compositions comprising an MP of the present invention.

3 Claims, 15 Drawing Sheets

U.S. PATENT DOCUMENTS

| | | | | |
|---|---|---|---|---|
| 4,404,128 | A | 9/1983 | Anderson | 252/546 |
| 4,533,359 | A | 8/1985 | Kondo et al. | 8/128 R |
| 4,816,587 | A | 3/1989 | Cabilly et al. | 530/387 |
| 5,147,842 | A | 9/1992 | Lotz et al. | 424/94.61 |
| 5,204,015 | A | 4/1993 | Caldwell et al. | 252/174.12 |
| 5,264,366 | A | 11/1993 | Ferrari et al. | 435/252.21 |
| 5,314,692 | A | 5/1994 | Haarasilta et al. | 424/94.2 |
| 5,612,055 | A | 3/1997 | Bedford et al. | 424/442 |

FOREIGN PATENT DOCUMENTS

| | | |
|---|---|---|
| EP | 0 244 042 A | 11/1987 |
| EP | 0 134 267 | 8/1989 |
| EP | 0 369 817 A2 | 5/1990 |
| WO | WO95/14099 | 5/1995 |

OTHER PUBLICATIONS

EMBL/GENBANK Accession No. BACAPRJ, Markland et al., May 15, 2002.*

Wells, J.A., et al., 1983, "Cloning, sequencing, and secretion of *Bacillus amyloliquefaciens* subtilisin in *Bacillus subtitis* ", Nucleic Acids Research, 11(22), pp. 7911-7925.*

Jang, J.S., et al., 1992, "Molecular cloning of a subtilisin J gene from *Bacillus stearothermophilus* and its expression in *Bacillus subtulis*", Biochemical and Biophysical Research Communatizations, 184(1), pp. 277-282.*

Wahl, J.M., et al., 1987, "Molecular hybridization of immobilized nucleic acids: Theoretical concepts and practical considerations", Methods in Enzymology, vol. 152, pp. 399-407.*

Altschul, Stephen F. et al., " Basic Local Alignment Search Tool," J. Mol. Biol. 215:403-410, 1990.

Anagnostopoulos, C. et al., "Requirements for Transformation in *Bacillus subtilis*," J. Bacterlol., 81:741-746, 1961.

Bakhiet Nouna et al., "Studies on Transfection and Transformation of Protoplasts of *Bacillus larvae*, *Bacillus subtilis*, and *Bacillus popilliae*," Appl. Environ. Microbiol., vol. 49, No. 3, pp. 577-581, 1985.

Chang, Shing et al. "High Frequency Transformation on *Bacillus subtilis* Protoplasts by Plasmid DNA," Mol. Gen. Genet. 168:111-115, 1979.

Contente, Sara et al., "Marker Rescue Transformation by Linear Plasmid DNA in *Bacillus subtilis*," Plasmid, 2:555-571, 1979.

Fischer, Hans-Martin et al., "Introduction of plasmid pC149 into *Baciilus thuringlensis* by protoplast transformation and plasmid transfer," Arch. Microbiol., 139:213-217, 1981.

Fujimura-Kamada, Konomi et al., "A Novel Membrane-associated Metalloprotease, Ste24p, Is Required for the First Step of $NH_2$-erminal Processing of the Yeast a-Factor Precursor," J. Cell. Biol. 138:271-285, 1997.

Haima, Peter., et al., "Novel plasmid marker rescue transformation system for moelcular cloning in *Bacillus subtilis* enabling direct selection of recombinants," Mol. Gen. Genet. 223:185-191, 1990.

Hotubova, I. et al. "Transfer of Liposome-Encapsulated Plasmid DNA to *Bacillus subtilis* Protoplasts and Calcium-Treated *Escherichia coli* Cells," Folia Microbiol., vol. 30, pp. 97-100, 1985.

Kroll, David J. et al., "A Multifunctional Prokaryotic Protein Expression System: Overproduction, Affinity Purification, and Selective Detection," DNA Cell Biol., vol. 12, No. 5, pp. 441-453, 1993.

Maddox, D. E. et al., "Elevated Serum Levels in Human Pregnancy of a Molecule Immunochemically Similar to Eosinophil Granule Major Basic Protein," J. Exp. Med., vol. 158, pp. 1211-1226, Oct. 1983.

Mann, Stephen P. et al., Transformation of *Bacillus spp.*: an Examination of the Transformation of Bacillus Protoplasts by Plasmids pUB110 and pHV33, Current Microbiol., vol. 13, pp. 191-195, 1986.

McDonald, Karen Orzech et al., "Plasmid Transformation of *Bacillus sphaericus* 1593," Journal of General Microbiology, vol. 130, pp. 203-208, 1984.

Murray, Elizabeth E. et al., "Codon usage in plant genes," Nucleic Acids Research, vol. 17, No. 2, pp. 477-498, 1989.

Ogasawara, Naotake et al., "Systematic sequencing of the *Bacillus sublitis* genome: progress report of the Japanese group," Microbiology, vol. 141, pp. 257-259, 1995.

Porath, Jerker, "Immobilized Metal Ion Affinity Chromatography," Protein Expression and Purification, vol. 3, pp. 263-281, 1992.

Smith, Hilde et al. "Characterization of signal-sequence-coding regions selected from the *Bacillus sublitis* chromosome," Gene, vol. 70, pp. 351-361, 1988.

Smith, Michael D. et al. "Protoplast Transformation in Coryneform Bacteria and Introduction of an α-Amylase Gene from *Bacillus amyloliquefaciens* into *Brevibacterium lactofermentum*," Applied and Environmental Microbiology, vol. 51, No. 3, pp. 634-639, Mar. 1986.

Vorobjeva, I. P. et al., "Transformation of *Bacillus Megaterium* Protoplasts by Plasmid DNA," FEMS Microbiology Letters, vol. 7, pp. 261-263, 1980.

Ward, Owen P., "Proteinases," Microbial Enzymes and Biotechnology, William Fogarty, ed., Applied Science Publishers, London and New York, pp. 251-317, 1983.

Weinrauch, Y. et al. "Plasmid Marker Rescue Transformation in *Bacillus subtilis*," Journal of Bacteriology, vol. 154, No. 3, pp. 1077-1087, Jun. 1983.

Weinrauch, Y. et al., "Plasmid Marker Rescue Transformation Proceeds by Breakage-Reunion in *Bacillus substilis*," Journal of Bacteriology, vol. 169, No. 3, pp. 1205-1211, Mar. 1987.

EMBL/GenBank Databases Accession No. Y14083, Sequence reference BSY14083, XP002094692.

Benton et al., "Steering λgt Recombinant Clones by Hybridization to Single Plaques in aitu," Science, vol. 198, No. 4288, pp. 180-182, Apr. 8, 1977.

Grunstein et al., "Colony hybridization: A method for the isolation of cloned DNAs that contain a specific gene," Proc. Nat. Acad. Sci. USA, vol. 72, No. 10, pp. 3961-3965, Oct. 1975.

* cited by examiner

```
CAGCATATCTTTGACGTGCTGTCTTTTTTCAATCTCTGATATCTTCCTGGCCGCTTGAAGA     60
GTCGTATAGAAACTGCACGACAGAAAAAAGTTAGAGCTATAGAAGGACCGGGAACTTCT

CAGTGTGATCAAATCCCGGCTACCGATTGATACACATCGCCTGATCGGCTGTAAAGATA    120
GTCACACTAGTTTAGGGCGATGCCAGATGGCTAACTATGTGTAGCGGACTAGCCGACATTTCTAT

AAAAAATGCGGATAAACACAAGACCGATTACCACGATGGCTGCCACTATTTTTTCATTTG    180
TTTTTTACGCTATTTGTGTTCTGGCTAATGGTGCTACCGACGGTGATAAAAAAGTAAAC

CATCACTCCAAACATTGTTAGTTTTTCCCAGGCGATCGGGGGTTCCATGCTTAAAAGGGTGG   240
GTAGTGAGGTTTGTAACAATCAAAAGGGTCGCTAGCCCCAAAGGTACGAATTTCCCACC

AAAAGTGCGGAACACAGCTTGGTTCTAAGAATTTGAATTTATGATTACAATAGAAGTAAC    300
TTTTCACGCCTTGTGTCGAACCAAGATTCTTAAACTTAAATACTAATGTTATCTTCATTG
```

FIG._1A-1

```
GGGTTGATGTGAGGAGTGAGGCGTTATGCGCAAGTGGATTGCGGGCAGCAGGACTTGCTTA
---------+---------+---------+---------+---------+---------+  360
CCCAACTACACTCCTCACTCCGCAATACGCGTTCACCTAACGCCGTCGTCCTGAACGAAT
                        M  R  K  W  I  A  A  G  L  A  Y
                        └──────────────────────────────
                                    yhfN CGTGCTGTACGGGCTGTTTTTTTATTGGTATTTTTTCCGTCGGGTGATTCCGCAATACC
---------+---------+---------+---------+---------+---------+  420
GCACGACATGCCCGACAAAAAAATAACCATAAAAAAGGCAGCCCACTAAGGCGTTATGG
  V  L  Y  G  L  F  F  F  Y  W  Y  F  F  L  S  G  D  S  A  I  P
─────────────────────────────────────────────────────────────
                          yhfN GGAAGCCCGTGAAAGGGACGGCAGGCTGATCCGGCTTCTTTCATGAAGCCGTCTGAGTTGGC
---------+---------+---------+---------+---------+---------+  480
CCTTCGGGCACTTTCCCTGCCGTCCGACTAGGCCGAAGAAAGTACTTCGGCAGACTCAACCG
  E  A  V  K  G  T  Q  A  D  P  A  S  F  M  K  P  S  E  L  A
─────────────────────────────────────────────────────────────
                          yhfN AGTGGCCGAGCAGTATTCGAATGTCAAGAATTTTTTATTTTTTATCGGGTACCACTTGA
---------+---------+---------+---------+---------+---------+  540
TCACCGGCTCGTCATAAGCTTACAGTTCTTAAAAAATAAAAAATAGCCCATGGTGAACT
  V  A  E  Q  Y  S  N  V  K  N  F  L  F  F  I  G  V  P  L  D
─────────────────────────────
            yhfN
```

FIG._1A-2

```
TTGGTTTCTGTTTTTGTTCTGCTTGTCAGCGGTGTTCAAAGAAATCAAGAAATGGAT
                                                                    + 600
AACCAAAGACAAAAACAAGAGAACAGTCGCCACAAAGTTTCTTTAGTTCTTTACCTA

W  F  L  F  F  V  L  L  V  S  G  V  S  K  K  I  K  K  W  I
                                 yhfN CGAAGCGGCCGTGCCTTTTCGGTTTTTGCAGAGACCGTTGGTTTTGTGTTTGTCTTTCGCT
                                                                    + 660
GCTTCGCCGGCACGGAAAAGCCAAAACACGTCTGGCAACCAAAACACAAAGAAAGCGA E  A  A  V  P  F  R  F  L  Q  T  V  G  F  V  F  V  L  S  L
                                 yhfN GATTACAACATTGGTGAACCACTGCCTTTAGAGATTGGATAGGCTATCAAGTATCGCTTGACTA
                                                                    + 720
CTAATGTTGTAACCACTGGCGACGGAAAATCTAACCTATCCGATAGTTCATAGCGAACTGAT I  T  T  L  V  T  L  P  L  D  W  I  G  Y  Q  V  S  L  D  Y
                                 yhfN TAACATTTCCACACAGACAACGGCCAGCTGGGCTAAGGATCAGGTTATCAGCTTTTGGAT
                                                                    + 780
ATTGTAAAGGTGTGTCTGTTGCCGGTCGACCGATTCCTAGTCCAATAGTCGAAACCTA N  I  S  I  Q  I  I  A  S  W  A  K  D  Q  V  I  S  F  W  I
                                 yhfN
```

FIG._1B-1

```
CAGCTTTCCAATCTTTACGCTTTGCGTTCTCGTTTTTATTGGCTGATCAAAGGCATGA
---+---------+---------+---------+---------+---------+-- 840
GTCGAAAGGTTAGAAATGCGAAACGCAAGAGCAAAAATAACCGACTAGTTTCCGTACT

S F P I F T L C V L V F Y W L I K R H E
                         yhiN

AAAAAATGGTGGTTATACGCCCTGGCTGTTAACAGTGCCGTTTTCGCTGTTTCTGTTTT
---+---------+---------+---------+---------+---------+-- 900
TTTTTTACCACCAATATGCGGACCGACAATTGTCACGGCAAAAGCGACAAAGACAAAA

K K W W L Y A W L L T V P F S L F F F
                         yhiN

TATTCAGCCGGTCATTATCGATCCTTTATACAATGATTTTTATCCGCTGAAAAACAAAGA
---+---------+---------+---------+---------+---------+-- 960
ATAAGTCGGCCAGTAATAGCTAGGAAATATGTTACTAAAAATAGGCGACTTTTTGTTTCT

I Q P V I I D P L Y N D F Y P L K N K E
                         yhiN

GCTTGAAAGCAAAATTTTAGAGCTGGCAGATGAAGCCAATATTCCGGCTGACCATGTATA
---+---------+---------+---------+---------+---------+-- 1020
CGAACTTTCGTTTTAAAATCTCGACCGTCTACTTCGGTTATAAGGCCGACTGGTACATAT

L E S K I L E L A D E A N I P A D H V Y
                         yhiN
```

FIG._1B-2

```
TGAAGTGAACATGTCAGAAAAAACAAATGCGCTGAATGCCTATGTTACAGGAATTGGGGC                1080
     +         +         +         +         +         +
ACTTCACTTGTACAGTCTTTTTTGTTTACGCGACTTACGGATACAATGTCCTTAACCCCG

E  V  N  M  S  E  K  T  N  A  L  N  A  Y  V  T  G  I  G  A
                          ─────────────────────────────────────
                                       yhfN CAATAAACGGATTGTATTGTGGGCCACGAAATGGGCCATTATGTCATGAAGCACGTTACATCGGTCTGGC      1140
     +         +         +         +         +         +
GTTATTTGCCTAACATAACACCCTATGCTGCACTTACCCGGTAATACAGTACTTCGTGCAAATGTAGCCAGACCG N  K  R  I  V  L  W  D  T  T  L  N  K  L  D  D  S  E  I  L
   ───────────────────────────────────────────────
                     yhfN GTTTATTATGGGCCACGAAATGGGCCATTATGTCATGAAGCACGTTACATCGGTCTGGC                1200
     +         +         +         +         +         +
CAAATAATACCCGGTGCTTTACCCGGTAATACAGTACTTCGTGCAAATGTAGCCAGACCG F  I  M  G  H  E  M  G  H  Y  V  M  K  H  V  Y  I  G  L  A
                          ─────────────────────────────────────
                                       yhfN TGGCTATTTGCTCGTGTCGCTCGCCGGATTTTATGTCATTGATAAGCTTTACAAGCGGAC                1260
     +         +         +         +         +         +
ACCGATAAACGAGCACAGCGAGCGGCCTAAAATACAGTAACTATTCGAAATGTTCGCCTG G  Y  L  L  V  S  L  A  G  F  Y  V  I  D  K  L  Y  K  R  T
   ─────────────────────────────────────
                   yhfN
```

FIG._1C-1

```
GGTTCGCCTAACCCGCAGCATGTTTCATTTAGAAGGGGGCATGATCTTGCGGCACTTCC
     ----+----|----+----|----+----|----+----|----+----|----+----|   1320
CCAAGCGGATTGGGCGTCGTACAAAGTAAATCTTCCCGCCGTACTAGAACGCCGTGAAGG

V  R  L  T  R  S  M  F  H  L  E  G  R  H  D  L  A  A  L  P
                                   yhfN GCTGTTATTGCTTTTTCTGTTTTTGAGCTTTGCGGTTACGCCTTTTTCTAATGCTGT
     ----+----|----+----|----+----|----+----|----+----|----+----|   1380
CGACAATAACGAAAACAGACAAAAACTCGAAACGCCAATGCGGAAAAAGATTACGACA L  L  L  L  F  S  V  L  S  F  A  V  T  P  F  S  N  A  V
                                   yhfN CTCGCGGTTATCAGGAGAATAAGGCTGACCAGTATGGGATCGAGTTGACAGAGAACAGAGA
     ----+----|----+----|----+----|----+----|----+----|----+----|   1440
GAGCGCCAATAGTCCTCTTATTCCGACTGGTCATACCCTAGCTCAACTGTCTCTTGTCTCT S  R  Y  Q  E  N  K  A  D  Q  Y  G  I  E  L  T  E  N  R  E
                                   yhfN AGCCGCTGTTAAAACGTTTCAGGATTGGGCCGTGAGGGCTGAGCCAGGTTGATCCTCC
     ----+----|----+----|----+----|----+----|----+----|----+----|   1500
TCGGCGACAATTTTGCAAAGTCCTAAACCGGCACTCCCGACTCGGTCCAACTAGGAGG A  A  V  K  T  F  Q  D  L  A  V  I  G  L  S  Q  V  D  P  P
                                   yhfN
```

FIG._1C-2

```
GGTGCTTGTGAAGATTTTCAGAGGCAGCCATCCGTCGATCATGGAACGGATTCAACATGC
     +         +         +         +         +         +     1560
CCACGAACACTTCTAAAAGTCTCCGTCGGTAGGCAGCTAGTACCTTGCCTAAGTTGTACG

V  L  V  K  I  F  R  G  S  H  P  S  I  M  E  R  I  Q  H  A
                                   yhfN GGAGAAAGAAGAGAAATGCGCCGGAACATCAGGATGCTGACAAATAAAAAGAAGCAGGTAT
     +         +         +         +         +         +     1620
CCTCTTTCTTCTCTTTACGCGGCCTTGTAGTCCTACGACTGTTTATTTTTCTTCGTCCATA E  K  E  E  N  A  P  E  H  Q  D  A  D  K
                       yhfN GGAGGAACCTGCTTCTTTTTACTATTATTGTGCAGCTGCCTTGTACGTTGATTAACCCTTT
     +         +         +         +         +         +     1680
CCTCCTTGGACGAAGAAAAATGATAATAACACGTCGACGGAACATGCAACTAATTGGGAAA TCCATAGTAGAAAGAGTTTCCAAGATATGTTGCAGTGCTTTCTAAACGATCACGGACTTG
     +         +         +         +         +         +     1740
AGGTATCATCTTTCTCAAAGGTTCTATACAACGTCACGAAAGATTGCTAGTGCCTGAAC CGCGTTTGTCCAAGTCGGGTGCTTAGAAAAGAATTAACGCTGCTGCTCCGGCAACGTGAGG
     +         +         +         +         +         +     1800
GCGCAAACAGGTTCAGCCCAGTCGGGTCTTTAAGAATCTTTCTTAATTGCGACGACGAGGCCGTTGCACTCC
```

FIG._1D-1

```
AGTCGCCATGGACGTTCCGTTATAAGCGCCGTAAGTGCCTCCAGGAAGTGTGCTTTGGAT
                                                             + 1860
TCAGCGGTACCTGCAAGGCAATATTCGCGGCATTCACGGAGGTCCTTCACACGAAACCTA

GGACACGCCAGGAGCCATCACATCAAGCTCAGAACCTGCGCTGGAGAATGAAGCTCTTTG
                                                             + 1920
CCTGTGCGGTCCTCGGTAGTGTAGTTCGAGTCTTGGACGCGACCTCTTACTTCGAGAAAC

GTTGCTGCTGTGTTACCGGCACCTACTGCAATAGTAGAAGGATATTTTGCAGGGTAGCCGAC
                                                             + 1980
CAACGACGACACAAATGGCGTGGATGACGTTATCATCTTCCTATAAAACGTCCCATCGGCTG

TGTGCTTGTGCTTCCGGATGAACCTTCGTTCCGGCTGCGCAGCAACGACGATACCGCT
                                                             + 2040
ACACGAACACGAAGGCCTACTTGGAAGCAAGGCCGACGCGTTGCTGCTATGGCGA

GGAAACGGCTTTGTCAACGACTGTTTCAGGCGCTGTAGAACCAGTAGGTCCGCCAAGGCT
                                                             + 2100
CCTTTGCCGAAACAGTTGCTGACAAAGTCGCGACATCTTGGTCATCCAGGCGGTTCCGA
```

FIG._1D-2

```
CATGTTGATAACATCCATATTGTTGGAAATGGCCCACTCAATGCCGTTAATAATCCAGCT
   ----+----+----+----+----+----+----+----+----+----+----+----+ 2160
GTACAACTATTGTAGGTATAACAACCTTTACCGGGTGAGTTACGGCAATTATTAGGTCGA

ATATTGGCCGCTTCCTGTTGAATCAAGCACTTTACTGCATATAATGATGCGCTTGGGCT
   ----+----+----+----+----+----+----+----+----+----+----+----+ 2220
TATAACCGGCGAAGGACAACTTAGTTCGTGAAAATGACGTATATTACTACGCGAACCCGA

AACGCCCAGAACACCGATTGAGTTATTAAGAGCGGCAATCGTACCGGCTACATGCGTACC
   ----+----+----+----+----+----+----+----+----+----+----+----+ 2280
TTGCGGGTCTTGTGGCTAACTCAATAATTCTCGCCGTTAGCATGGCCGATGTACGCATGG

GTGAGAACTGCCGTCCTGGTATGGGTTGTTTCAGAAGGTACGAAGCTTGCTCCGCCTCT
   ----+----+----+----+----+----+----+----+----+----+----+----+ 2340
CACTCTTGACGGCAGGACCATACCCAAACAAAGTCTTCCATGCTTCGAACGAGGCGGAGA

GACGTTTAAGTCAGGATGAGAAGAGTCAATTCCGCTGTCGATAACAGCTACTTTTACGTT
   ----+----+----+----+----+----+----+----+----+----+----+----+ 2400
CTGCAAATTCAGTCCTACTCTTCTCAGTTAAGGCGACACAGCTATTGTCGATGAAAATGCAA

AGAGCCTGTGTAGCCTTGAGAGTGAAGAGCCGGGCGCTTTAATTTGAGAAATGCCATAAGG
   ----+----+----+----+----+----+----+----+----+----+----+----+ 2460
TCTCGGACACATCGGAACTCTCACTTCTCGGCCCGCGAAATTAAACTCTTTACGGTATTCC
```

FIG._1E-1

```
AACAGATTGCGCATATTCATGTGCAATATGATCTTCTTCCACATATGCAACGCTCGGATC
----+----+----+----+----+----+----+----+----+----+----+----+  2520
TTGTCTAACGCGTATAAGTACACGTTATACTAGAGAAGGTGTATACGTTGCGAGCCTAG

TTTTTCAATTCTTTTACAGCTTTTTCATCCAATGTTGCTGCGCCGCGTTAACATACTT
----+----+----+----+----+----+----+----+----+----+----+----+  2580
AAAAAGTTAAGAAAAGTCGAAAAAGTAGGTTACAACGACGCCGGCAATTGTATGAA

AAATTGCTTTTGAACCCTTTCCGCCTTTTTCAGAAATAACATCCTTTTTCTTGGCGGAACT
----+----+----+----+----+----+----+----+----+----+----+----+  2640
TTTAACGAAAACTTGGAAAGGCGGAAAAAGTCTTTATTGTAGGAAAAAGAACCGCCTTGA

CATGGCACTTCATTGTCTCGTTAAATCCGACAATGTATTTCTTTTCTGTACTGCTTTTTCC
----+----+----+----+----+----+----+----+----+----+----+----+  2700
GTACCGTGAGTAACAGAGCAAATTTAGGCTGTTACATAAAGAAAAGACATGACGAAAAAGG

GGCAGCCTGCACAGACATGTTGCTGAACGCCATCGTAAAGATTAACGTTAACGCAAACAA
----+----+----+----+----+----+----+----+----+----+----+----+  2760
CCGTCGGACGTGTCTGTACAACGACTTGCGGTAGCATTTCTAATTGCAATTGCGTTTGTT
```

*FIG._1E-2*

```
SCSTE24.PRO    MMRILLFL-T-----------------NMAVM-VLGXILSXTGIPWKISIAGLSI--Y    27
AFC1_S-1.PRO   M------F-----------------------------DLKTILDHPNIPWKLIISGFSIAQF   60
HTPX_E-1.PRO   MSPGLCFLKEISVIQATPKPTTRSFANCCKMGILQHLMHILDIPGFPWKIVIAGFSIGKY   36
HTPX_H-1.PRO   MMRIALFLLT-------------------NLAVMVVFGLVLSLTGIQ-SSSVQGL-----   36
YHFN.PRO       MMRILLFLAT-------------------NMAVMLVLGIILSVTGIA-GNSTGGI-----   36
               MRK------------------------------------------W-IAAAGLAYVLY    15
                        10        20        30        40        50        60

SCSTE24.PRO    SFESYLTYRQYQKLSETKLPPVLEDEIDDETFHKSRNYSRAKAKFSIFGDVYNLAQKLVF   87
AFC1_S-1.PRO   AWDLYLRRRQVPYLLREKPPAILAEHVDEKKYQKALSYARDKSWFSTIVSTFTLAVDLLI  120
HTPX_E-1.PRO   ---YL--------L------KPPAVL----D---F-K---YA-------MIMALF     42
HTPX_H-1.PRO   ---------------------------------------------------LIMALF     42
YHFN.PRO       GLFFYWYF--FLSGDSAIPEAVKGTQADPASFMKPSELA----------VAEQYSNVKNFLF  65
                                                              Y-LAMALLF
                        70        80        90       100       110       120

SCSTE24.PRO    IKYDLFPKIWHMAVSLLNAVLPV--REHMVST---VAQSLCFLGLLSSLSTLVDLPLSY   141
AFC1_S-1.PRO   IKYDGLSYLMNITKFPWMDKLAASSSRFSLSTS---ITHSCVFMFGLTLFSRLIQIPFNL   177
HTPX_E-1.PRO   ----------------RF--------------------GFGGGFVSLLMSKWMALRS    61
HTPX_H-1.PRO   ----------------------------------------GFAGSLISLFLSKTMALRS    61
YHFN.PRO       --FIGVPLDWFLFFVLLVSGVSKKIKKWIEAAVPFRFLQTVGFVFVLSITTLVTLPLDW   123
               --YDG-P--W----LL----L------RF---------QS-GFXGSLSSLSTLVTLPLRS
                       130       140       150       160       170       180
```

FIG._2A-1

```
            VGGEVIEEKYGFNKNTTERWLIDTVKSL-L----I----V-VF-KI--KF---F--YAW--
             190       200       210       220       230       240
SCSTE24.PRO  YSHFVLEEKFGFNKLTVQLWITDMIKSLTLAYAIGGPILYLFLKIFDKFPTDFLWYIMVE  201
AFC1_S-1.PRO YSTFVIEEKYGFNKSTLKIFVIDLLKELSLGGLLMSVVVGFVKILTKFGDNFIMYAWGA  237
IITPX_E-1.PRO VGGEVIEQ-----PRNERERWLVNTVAT--------------------------------   85
HTPX_H-1.PRO VDGEVITQ-----PRNQTERWLIDTVSR--------------------------------   85
YHFN.PRO     IG-YQVSLDYNISTQTTASWAKDQVISFWISFPIFTLCVLVFYWLIKRHEKKWWLYAWLL  182

--VF-L--L--TI--PV-IMPLFNKFTPLENGEL---IEALAAGINFPLVAIYVID-S-HSPD
               250       260       270       280       290       300
SCSTE24.PRO  LFVVQILAMTIIPVFIMPMENKFTPLEDGELKKSIESLADRVGEPLDKIFVIDGSKRSSH  261
AFC1_S-1.PRO YIVFGLILQTIAPSLIMPLFYKFTPLENGSLRTQIEELAASINFPLKKLYVIDASRRSTH  297
IITPX_E-1.PRO --------------------------------QARQAGIAMPQVAIY-----HAPD----  103
HTPX_H-1.PRO --------------------------------QAQKAGIPMPDVAIY-----HSPD----  103
YHFN.PRO     TVPFSLFLFFIQPVIIDPLYNDFYPLKNKELESKILELADEANIPAUHVYEVNMSEKTNA  242

SNAFATGAPXXNKLIVLSDTLLNNMSEDEAEAVLAHEIGHIXNGHMVTNTLIQGGLNTFV
              310       320       330       340       350       360
SCSTE24.PRO  SNAYFTGLPFTSKRIVLFDTLVNSNSTDEITAVLAHEIGHWQKNH-IVNMVIFSQLHTFL  320
AFC1_S-1.PRO SNAFFYGLPW-NKGIVLFDTLVKNHTEPELIAILGHELGHWYMSHNLINTIIDYGMSLFH  356
IITPX_E-1.PRO INAFATGARRDASLVAVSTGLLQNMSPDEAEAVIAHEISHIANGDMVTNTLIQGVVNTFV  163
HTPX_H-1.PRO VNAFATGATKSNSLVAVSTGLLNNMTEAEAEAVLAHEISHISNGDMVTMALLQGVLNTFV  163
YHFN.PRO     LNAYVTGIG-ANKRIVLWDTTLNKLDDSEILFIMGHEMGHYVMKH-----VYIGLAGYL  295
```

FIG._2A-2

```
              IF-L-A-FYRSRLYTXFXFFLEKSRXXXEEXXXXXXIPFLVGLVLFSDLLGVLASIITF
SCSTE24.PRO   IFSLFTSIYRNTSFYNTFGFFLEKSTGSFVDPVITKEFPIIGFMLENDLLTPLECAMQF  380
AFC1_S-1.PRO  LF-LFAAFIRNNSLYTSFNFITEK--------------PVIVGLLLFSDALGPLSSILTF  401
HTPX_E-1.PRO  IF------ISRILAQLAAGFMGGNRDEGEESNGNPLIYFAVATVL-ELVFGILASIITM  215
HTPX_H-1.PRO  IF------LSRVIATA----VASSRNNNGEETRSSGIYFLVSMVL-EMLFGVLASIIAM  211
YHFN.PRO      LVSL-AGFYVIDKLYKR-TVRLTRSMFHLEGRHDLAALPLL--LLLFS-----VLSFAVTP  347
                      370        380        390        400        410        420

FIG._2A-3

-SNWVSRYREFQADAGAAKLGGKEKL-IXALQRLQXXNLSQXXDSLYASYINSHPXLXS
SCSTE24.PRO   VMSLISRTHEYQADAYAKKLGYKQNLC-RALIDLQIKNLSTMNVDPLYSSYHYSHPTLAE  439
AFC1_S-1.PRO  ASNKVSRLCEYQADAFAKQLGYAKDLG-DGLIRIHDDNLSPLEFDSLYTSYYHSHPILVD  460
HTPX_E-1.PRO  ---WFSRHREFHADAGSAKLVGREKM-IAALQRLKTSYEPQE-ATSMMALCINGKSKSLS  270
HTPX_H-1.PRO  ---WFSRYREFRADAGSASLVGKEKM-IMALQRLQQLHEPQNLEGSLNAFMINGKR---S  264
YHFN.PRO      FSNAVSRYQENKADQYGIFLTENREAAVKTFQDLAVTGLSQVDPPVLVKIFRGSHPSIME  407
                      430        440        450        460        470        480

RL----FMS-------HPNLEKEIEALRX--A-K
SCSTE24.PRO   RLTALDYVSEKKKNTHEABVEREPRTINFRMAT.               473
AFC1_S-1.PRO  RLNAIDYTTLKK-----N---------------N              474
HTPX_E-1.PRO  EL----FMT-------HPPLDKRIEALRTGEYLK               293
HTPX_H-1.PRO  EL----FMS-------HPPLEKRIEALRN----L               283
YHFN.PRO      RIQ-------------HAEKEENAPEHQDADK                 426
                      490        500        510

FIG._2B
```

```
Score = 1076 (498.2 bits), Expect = 3.7e-145, P = 3.7e-145
Identities = 209/229 (91%), Positives = 210/229 (91%), Frame = -1

Query:   198  IDPLYNDFYPLKNKELESKILELADEANIPADHVYEVNMSEKTNALNAYVTGIGANKRIV   257
              +DPLYNDFYPLKNKELESKILELADEANIPADHVYEVNMSEKTNALNAYVTGIGANKRIV
Sbjct:  2482  VDPLYNDFYPLKNKELESKILELADEANIPADHVYEVNMSEKTNALNAYVTGIGANKRIV  2303

Query:   258  LWDTTLNKLDDSEILFIMGHEMGHYVMKHVYIGLAGYLLVSLAGFYVIDKLYKRTVRLTR   317
              LWDTTLNKLDDSEILFIMGHEMGHYVMKHVYIGLAGYLLVSLAGFYVIDKLYKRTVRLTR
Sbjct:  2302  LWDTTLNKLDDSEILFIMGHEMGHYVMKHVYIGLAGYLLVSLAGFYVIDKLYKRTVRLTR  2123

Query:   318  SMFHLEGRHDXXXXXXXXXXXXXXXTPFSNAVSRYQENKADQYGIELTENREAAVKT    377
              SMFHLEGRHD                 TPFSNAVSRYQENKADQYGIELTENREAAVKT
Sbjct:  2122  SMFHLEGRHDLVALPLLLLFSVLSFAVTPFSNAVSRYQENKADQYGIELTENREAAVKT  1943

Query:   378  FQDLAVTGLSQVDPPVLVKIFRGSHPSIMERIQHAEKEENAPEHQDADK             426
              FQDLAVTGLSQVDPPVLVKIFRGSHPSIMERIQH EKEENAPEHQDADK
Sbjct:  1942  FQDLAVTGLSQVDPPVLVKIFRGSHPSIMERIQHTEKEENAPEHQDADK             1796
```

FIG._3

```
Score = 211 (97.7 bits), Expect = 1.9e-27, Sum P(2) = 1.9e-27
Identities = 40/42 (95%), Positives = 40/42 (95%), Frame = -1

Query:   385  GLSQVDPPVLVKIFRGSHPSIMERIQHAEKEENAPEHQDADK  426
              G QVDPPVLVKIFRGSHPSIMERIQHAEKEENAPEHQDADK
Sbjct:  1449  GAEQVDPPVLVKIFRGSHPSIMERIQHAEKEENAPEHQDADK  1324

Score = 95 (44.0 bits), Expect = 1.9e-27, Sum P(2) = 1.9e-27
Identities = 19/22 (86%), Positives = 22/22 (100%), Frame = -2

Query:   368  TENREAAVKTFQDLAVTGLSQV  389
              TENREA+VKTFQDLAVTGLS++
Sbjct:  1499  TENREASVKTFQDLAVTGLSRL  1434
```

FIG._6

```
Score = 469 (217.1 bits), Expect = 1.1e-79, Sum P(3) = 1.1e-79
Identities = 90/116 (77%), Positives = 100/116 (86%), Frame = -1

Query:   212  ELESKILELADEANIPADHVYEVNMSEKTNALNAYVTGIGANKRIVLMDTTLNKLDDSEI 271
              +LE  IL+LAD+A+IPA+HVYEVNMSEKTNALNAYVTGIGANKRIVLMDTTLNKLD+ EI
Sbjct:   2044 DLEQSILKLADQADIPANHVYEVNMSEKTNALNAYVTGIGANKRIVLMDTTLNKLDEPEI 1865

Query:   272  LFIMGHEMGHYYVMKHVYIGLAGYLLLVSLAGFYVIDKLYKRTVRLTRSMFHLEGRHD 327
              LFIM HEMGHYVMKHVYIGL GYLL+SLA FYVIDKLYKR +        H+ G+ D
Sbjct:   1864 LFIMAHEMGHIYVMKHVYIGLGGYLLLSLAVFYVIDKLYKRIIGRYGKSLHIAGKSD 1697

Score = 124 (57.4 bits), Expect = 1.1e-79, Sum P(3) = 1.1e-79
Identities = 24/46 (52%), Positives = 34/46 (73%), Frame = -3

Query:   369  ENREAAVKTFQDLAVTGLSQVDPPVLKIFRGSHPSIMERIQHAEK 414
              E+   + TFQ+L+   GLS+ +PP LVKIF+    HP+IMERIQ+ E+
Sbjct:   1574 EHTMQRLPTFQELSKAGLSEANPPFLVKIFKYGHPTIMERIQNIEQ 1437

Score = 77 (35.7 bits), Expect = 1.1e-79, Sum P(3) = 1.1e-79
Identities = 14/21 (66%), Positives = 18/21 (85%), Frame = -2

Query:   346  TPFSNAVSRYQENKADQYGIE 366
              +PF+NAVSR+QE  ADQY I+
Sbjct:   1641 SPFTNAVSRHQEKAADQYAID 1579
```

FIG._4

```
Score = 291 (134.7 bits), Expect = 8.1e-31, P = 8.1e-31
Identities = 56/70 (80%), Positives = 64/70 (91%), Frame = -3

Query:   347  PFSNAVSRYQENKADQYGIELTENREAAVKTFQDLAVTGLSQVDPPVLKIFR 
              P  NAVSRYQEN AD+YGIELT NREAA++TFQDLAV GLS+V+PP LVKIFR
Sbjct:   1848 PIRNAVSRYQENAADRYGIELTGNREAAIETFQDLAVRGLSRVNPPFLVKIFR Query:   407  ERIQHAEKEE 416
              ERI+HAE+E+
Sbjct:   1668 ERIEHAEEEK 1639
```

PROTEASES FROM GRAM-POSITIVE ORGANISMS

This is a Continuation of U.S. patent application Ser. No. 10/328,459, filed Dec. 23, 2002, now U.S. Pat. No. 6,905,868, which is a Divisional of U.S. patent application Ser. No. 09/486,192, filed on Feb. 22, 2000, issued as U.S. Pat. No. 6,521,440 on Feb. 18, 2003, which is a 371 of PCT/US98/18677 filed Sep. 8, 1998, which in turn claims priority to UK Application no. GB9719637.2, filed Sep. 15, 1997.

FIELD OF THE INVENTION

The present invention relates to metallo-proteases derived from gram-positive microorganisms. The present invention provides nucleic acid and amino acid sequences of metallo-proteases identified in *Bacillus*. The present invention also provides methods for the production of the metallo-protease in host cells as well as the production of heterologous proteins in a host cell having a mutation or deletion of part or all of metallo-proteases of the present invention.

BACKGROUND OF THE INVENTION

Gram-positive microorganisms, such as members of the group *Bacillus*, have been used for large-scale industrial fermentation due, in part, to their ability to secrete their fermentation products into the culture media. In gram-positive bacteria, secreted proteins are exported across a cell membrane and a cell wall, and then are subsequently released into the external media usually maintaining their native conformation.

Various gram-positive microorganisms are known to secrete extracellular and/or intracellular protease at some stage in their life cycles. Many proteases are produced in large quantities for industrial purposes. A negative aspect of the presence of proteases in gram-positive organisms is their contribution to the overall degradation of secreted heterologous or foreign proteins.

The classification of proteases found in microorganisms is based on their catalytic mechanism which results in four groups: the serine proteases; metallo-proteases; cysteine proteases; and aspartic proteases. These categories can be distinguished by their sensitivity to various inhibitors. For example, the serine proteases are inhibited by phenylmethylsulfonylfluoride (PMSF) and diisopropylfluorophosphate (DIFP); the metallo-proteases by chelating agents; the cysteine enzymes by iodoacetamide and heavy metals and the aspartic proteases by pepstatin. The serine proteases have alkaline pH optima, the metalloproteases are optimally active around neutrality, and the cysteine and aspartic enzymes have acidic pH optima (*Biotechnology Handbooks, Bacillus*. vol. 2, edited by Harwood, 1989 Plenum Press, New York).

Metallo-proteases form the most diverse of the catalytic types of proteases. About half of the families comprise enzymes containing the His-Glu-Xaa-Xaa-His (or HEXXH) motif which has been shown by X-ray crystallography to form part of the site for binding of the metal (normally zinc) atom. In one family of metalloproteases, a glutamic acid residue completes the metal-binding site, HEXXH+E. This family contains the most well characterized of the metalloproteases, thermolysin. The three dimensional structure of thermolysin shows that, in the HEXXH motif, the His residues are zinc ligands and the Glu residue has a catalytic function. (Methods in Enzymology, vol. 248, Academic Press, Inc. 1994).

Fujimura-Kamada et al. (1997, J. Cell Biol. 136: 271-285) disclose a new subfamily of proteins that appear to function as intracellular, membrane-associated zinc metalloproteases. They disclose the *Saccharomyces cerevisiae* STE24 gene product which contains a zinc metalloprotease motif (HEXXH), as well as multiple predicted membrane spans. They further disclose that STE24 is required for the first NH2-terminal proteolytic cleavage event during biogenesis of the a-factor precursor.

SUMMARY OF THE INVENTION

The present invention relates to the discovery of a heretofore unknown metallo-protease (MP) found in gram positive microorganisms, uses of the MP in industrial applications, and advantageous strain improvements based on genetically engineering such microorganisms to delete, underexpress or overexpress that MP. The present invention is based in part upon the discovery that MP has overall amino acid relatedness to *S. cerevisiae* STE24 (Fujimura-Kamada et al., supra) and in part upon the unexpected discovery that nucleic acid encoding gram positive microorganism MP is found immediately downstream of nucleic acid encoding the major alkaline protease putative transcriptional terminator in gram-positive microorganisms.

The present invention is also based, in part, upon Applicant's discovery that the characteristic metallo-protease amino acid motif HEXXH+E and putative transmembrane domains exist in *Bacillus subtilis* MP. The present invention is also based in part upon Applicant's discovery that *Bacillus subtilis* MP homologs are found in *Bacillus subtilis, Bacillus stearothermophilus, Bacillus licheniformis* and *Bacillus amyloliquifaciens*. Applicant's discovery, in addition to providing a new and useful group of proteases and methods of detecting DNA encoding such proteases in a gram positive microorganism, provides several advantages which may facilitate optimization and/or modification of strains of gram positive microorganisms, such as *Bacillus*, for expression of desired, e.g. heterologous, proteins. Such optimizations, as described below in detail, allow the construction of strains having decreased proteolytic degradation of desired expression products.

Due to the relatedness of MP to STE24, a zinc metalloprotease which has been shown to be involved in processing events, and the unexpected conserved structural arrangement and proximity of gram positive MPs to the major alkaline protease of multiple *Bacillus* species, it appears that MP may play a role in regulating and/or processing the major alkaline protease in *Bacillus*. Furthermore, MP can serve as a marker for identification of the major alkaline protease in *Bacillus* species.

In one embodiment, the metallo-protease is derived from a gram-positive microorganism which is a *Bacillus*. In another embodiment, the metallo-protease is derived from a *Bacillus* which is preferably selected from the group consisting of *Bacillus subtilis, Bacillus stearothermophilus, Bacillus licheniformis* and *Bacillus amyloliquifaciens*. The present invention encompasses the naturally occurring MP encoded by nucleic acid found immediately downstream from the transcriptional terminator of the major alkaline protease of a *Bacillus* species as well as the nucleic acid and amino acid molecules having the sequences disclosed in the Figures.

In a preferred embodiment, the present invention encompasses the naturally occurring MP nucleic acid molecule having the sequence found in *Bacillus subtills* I-168 strain (Bacillus Genetic Stock Center, accession number 1A1, Columbus, Ohio) In the region of about 1102 kb from the point of origin and immediately downstream of the putative transcriptional terminator of the aprE gene. In another preferred embodiment, the *Bacillus subtilis* MP nucleic acid and amino acid molecules have the sequences as shown in FIGS. 1A-1E (SEQ ID NO:1 and SEQ ID NO:2, respectively).

The present invention is also based in part upon the unexpected discovery of nucleic acid encoding portions of *Bacillus subtilis* MP homologs found in at least 3 non *B. subtilis Bacillus* species, including *Bacillus stearothermophilus, Bacillus licheniformis* and *Bacillus amyloliquifaciens*. The *Bacillus stearothermophilus, Bacillus licheniformis* and *Bacillus amyloliquifaciens* MP is found downstream of the major alkaline protease of each *Bacillus*.

The present invention encompasses the naturally occurring *Bacillus stearothermophilus, Bacillus licheniformis* and *Bacillus amyloliquifaciens* MP. In a preferred embodiment, the MP is encoded by the nucleic acid molecules having the nucleic acid sequence that is immediately downstream of the putative transcriptional terminator of the major alkaline protease or subtilisn in the genome of *Bacillus stearothermophilus, Bacillus licheniformis* or *Bacillus amyloliquifaciens*.

In one preferred embodiment, the *Bacillus stearothermophilus* MP comprises the amino acid sequence as shown in FIG. 3. In another preferred embodiment, the *Bacillus licheniformis* MP comprises the amino acid sequence as shown in FIG. 4. In another preferred embodiment, the *Bacillus amyloliquifaciens* MP comprises the amino acid sequence as shown in FIG. 5. The present invention encompasses any nucleic acid molecule encoding *Bacillus stearothermophilus, Bacillus licheniformis* or *Bacillus amyloliquifaciens* MP.

The present invention provides isolated polynucleotide and amino acid sequences for *Bacillus subtilis* MP in FIGS. 1A-1E (SEQ ID NO:1 and SEQ ID NO:2, respectively). Due to the degeneracy of the genetic code, the present invention encompasses any nucleic acid sequence that encodes the *Bacillus subtilis* MP amino acid sequence. The present invention provides expression vectors and host cells comprising nucleic acid encoding a gram-positive MR The present invention also provides methods of making the gram positive MP.

The present invention encompasses novel amino acid variations of gram positive MP amino acid sequences disclosed herein that have proteolytic activity. Naturally occurring gram positive MP as well as proteolytically active amino acid variations or derivatives thereof, have application in the textile industry, in cleaning compositions and in animal feed.

The present invention provides methods for detecting gram positive microorganism homologs of *B. subtilis* MP that comprises hybridizing part or all of the nucleic acid encoding *B. subtilis* MP with nucleic acid derived from gram-positive organisms, either of genomic or cDNA origin. Accordingly, the present invention provides a method for detecting a gram-positive microorganism MP, comprising the steps of hybridizing gram-positive microorganism nucleic acid under low stringency conditions to a probe, wherein the probe comprises part or all of the nucleic acid sequence shown in FIGS. 1A-1E (SEQ ID NO:1; and isolating gram-positive nucleic acid which hybridizes to said probe.

Based upon the genomic proximity of MP to the major alkaline protease, the present invention provides a means of detecting the major alkaline protease of gram-positive microorganisms species based upon nucleic acid hybridization to *B. subtilis* MP. In one embodiment, the gram-positive microorganism is a *Bacillus*. In another preferred embodiment, the *Bacillus* is selected from the group consisting of *B. licheniformis, B. lentus, B. brevis, B. stearothermophilus, B. alkalophilus, B. amyloliquefaciens, B. coagulans, B. circulans, B. lautus* and *Bacillus thuringiensis*.

The production of desired heterologous proteins or polypeptides in gram-positive microorganisms may be hindered by the presence of one or more proteases which degrade the produced heterologous protein or polypeptide. One advantage of the present invention is that it provides methods and expression systems which can be used to prevent that degradation, thereby enhancing yields of the desired heterologous protein or polypeptide.

Accordingly, the present invention provides a gram-positive microorganism having a mutation or deletion of part or all of the gene encoding MP, which results in the inactivation of the MP proteolytic activity, either alone or in combination with mutations in other proteases, such as apr, npr, epr, mpr, bpf or isp for example, or other proteases known to those of skill in the art. In one embodiment of the present invention, the gram-positive organism is a member of the genus *Bacillus*. In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *Bacillus thuringiensis*. In a further preferred embodiment, the *Bacillus* is *Bacillus subtilis*.

The present invention also encompasses amino acid variations or derivatives of gram positive MP that do not have the characteristic proteolytic activity as long as the nucleic acid sequences encoding such variations or derivatives would have sufficient 5' and 3' coding regions to be capable of being integrated into a gram-positive organism genome. Such variants would have applications in gram-positive expression systems where it is desirable to delete, mutate, alter or otherwise incapacitate the naturally occurring metallo-protease in order to diminish or delete its proteolytic activity. Such an expression system would have the advantage of allowing for greater yields of recombinant heterologous proteins or polypeptides.

In another aspect, the gram-positive host having one or more metallo-protease deletions or mutations is further genetically engineered to produce a desired protein. In one embodiment of the present invention, the desired protein is heterologous to the gram-positive host cell. In another embodiment, the desired protein is homologous to the host cell. The present invention encompasses a gram-positive host cell having a deletion, mutation or interruption of the nucleic acid encoding the naturally occurring homologous protein, such as a protease, and having nucleic acid encoding the homologous protein re-introduced in a recombinant form. In another embodiment, the host cell produces the homologous protein. Accordingly, the present invention also provides methods and expression systems for reducing degradation of heterologous proteins produced in gram-positive microorganisms. The gram-positive microorganism may be normally sporulating or non-sporulating. In a preferred embodiment, the gram positive host cell is a *Bacillus*. In another preferred embodiment, the *Bacillus* host cell is *Bacillus*. In another embodiment, the *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *Bacillus thuringiensis*.

Naturally occurring gram positive MP as well as proteolytically active amino acid variations or derivatives thereof, have application in the textile industry, in cleaning compositions and in animal feed. The metallo-protease MP may be used alone or in combination with other enzymes and/or mediators or enhancers.

Accordingly, the present invention provides a cleaning composition comprising a metalloprotease of the present invention having the amino acid sequence shown in FIGS. 1A-1E (SEQ ID NO:2) or the amino acid encoded by the MP nucleic acid found at about 1102 kilobases from the point of origin of *Bacillus subtilis*. Also provided are cleaning compositions comprising a metalloprotease having at least 80%, at least 90%, or at least 95% homology with the amino acid sequence shown in FIGS. 1A-1E (SEQ ID NO:2) or comprising a metalloprotease encoded by a gene that hybridizes with the nucleic acid shown in FIGS. 1A-1E (SEQ ID NO:1) under high stringency conditions.

Further there is provided an animal feed comprising a metalloprotease, MP, having the amino acid sequence shown in FIGS. 1A-1E. Also provided are animal feeds comprising a metalloprotease having at least 80%, at least 90%, and at least 95% homology with the amino acid sequence shown in FIGS. 1A-1E or comprising a metalloprotease encoded by a gene that hybridizes with the nucleic acid shown in FIGS. 1A-1E under high stringency conditions.

Also provided is a composition for the treatment of a textile comprising a metalloprotease, MP, having the amino acid sequence shown in FIGS. 1A-1E (SEQ ID NO:2), Also provided are compositions for the treatment of a textile comprising a metalloprotease having at least 80%, at least 90%, or at least 95% homology with the amino acid sequence shown in FIGS. 1A-1E (SEQ ID NO:2) or comprising a metalloprotease encoded by a gene that hybridizes with the nucleic acid shown in FIGS. 1A-1E (SEQ ID NO:1) under high stingency conditions.

In a further aspect of the present invention, a Gram-positive MP is produced on an industrial fermentation scale in a microbial host expression system.

BRIEF DESCRIPTION OF THE DRAWINGS

FIGS. 1A-1E shows the DNA (SEQ ID NO:1), and amino acid sequence (SEQ ID NO:2), for *Bacillus subtilis* MP.

FIGS. 2A-2B show an amino acid alignment of *S. cerevisiae* STE24 (SEQ ID NO:3); *Bacillus subtilis* MP, designated as YHFN.PRO (SEQ ID NO:2); AFC1_S-1.PRO from *Schizosaccharomyces pombe* (Gentles S. EMBL Z68144; E212537 (SEQ ID NO:4)); HTPX_E-1.PRO (Koonin E. 1995, Proc. Natl. Acad. Sci U.S.A. 92:11921-11925 (SEQ ID NO:5)); and HTPX_H-1.PRO (1995 Science 269: 496-512 (SEQ ID NO:6)). The amino acid motif HEXXH +E is noted in FIGS. 2A-2B, 3 and 4.

FIG. 3 shows an amino acid alignment of MP with *Bacillus stearothermophilus* subtilisn J.

FIG. 4 shows an amino acid alignment of MP with *Bacillus licheniformis* alkaline protease.

FIG. 5 shows and amino acid alignment of MP with *Bacillus amyloliquifaciens* alkaline protease gene.

FIG. 6 shows the amino acid alignment of MP with *Bacillus subtilis* subtilisn.

DETAILED DESCRIPTION OF THE PREFERRED EMBODIMENTS

Definitions

As used herein, the genus *Bacillus* includes all members known to those of skill in the art, including but not limited to *B. subtilis, B. licheniformis, B. lentus, B. brevis, B. stearothermophilus, B. alkalophilus, B. amyloliquefaciens, B. coagulans, B. ciculans, B. lautus* and *B. thuringiensis*.

The present invention relates to a newly characterized metallo-protease (MP) from gram positive organisms. In a preferred embodiment, the gram-positive organisms is a *Bacillus*. In another preferred embodiment, tile *Bacillus* is selected from the group consisting of *B. subtilis, B. licheniformis, B. lentus, B. brevis, B. stearothermophilus, B. alkalophilus, B. amyloliquefaciens, B. coagulans, B. ciculans, B. lautus* and *B. thuringiensis*.

In another preferred embodiment, the gram-positive organism is *Bacillus subtilis* and MP has the amino acid sequence encoded by the nucleic acid molecule having the sequence that occurs around 1102 kilobases from the point of origin of *Bacillus subtilis* I-168. In one embodiment, nucleic acid encoding the *B. subtilis* MP is immediately downstream from the aprE putative transcriptional terminator.

In another preferred embodiment, *Bacillus subtilis* has the nucleic acid end amino acid sequence as shown in FIGS. 1A-1E (SEQ ID NO:1 and SEQ ID NO:2, respectively). The present invention encompasses the use of amino acid variations of the amino acid sequences disclosed in FIGS. 1A-1E that have proteolytic activity. Such proteolytic amino acid variants can be used in the textile industry, animal feed and in cleaning compositions. The present invention also encompasses the use of *B. subtilis* amino acid variations or derivatives that are not proteolytically active. DNA encoding such variants can be used in methods designed to delete or mutate the naturally occurring host cell MP.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homolog" as used herein refers to a gram-positive microorganism polynucleotide that has at least 80%, at least 90% and at least 95% identity to *B. subtilis* MP, or which is capable of hybridizing to *B. subtilis* MP under conditions of high stringency and which encodes an amino acid sequence having metallo-protease activity.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a given gram-positive host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a given gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

As used herein, the term "overexpressing" when referring to the production of a protein in a host cell means that the protein is produced in greater amounts than its production in its naturally occurring environment.

As used herein, the phrase "proteolytic activity" refers to a protein that is able to hydrolyze a peptide bond. Enzymes having proteolytic activity are described in Enzyme Nomenclature, 1992, edited Webb Academic Press, Inc.

DETAILED DESCRIPTION OF THE PREFERRED EMBODIMENTS

The unexpected discovery of the metallo-protease MP found in translated uncharacterised *B. subtilis* genomic sequences provides a basis for producing host cells, expression methods and systems which can be used to prevent the degradation of recombinantly produced heterologous proteins.

Accordingly, in a preferred embodiment, the host cell is a gram-positive host cell that has a deletion or mutation in the naturally occurring nucleic acid encoding MP said mutation resulting in deletion or inactivation of the production by the host cell of the MP proteolytic gene product. The host cell may additionally be genetically engineered to produced a desired protein or polypeptide.

Furthermore, due to the conserved proximity of MP to the major alkaline protease in *Bacillus*, MP may also be involved in regulation/processing of the major alkaline protease and can serve as a marker for the detection of the major alkaline protease of *Bacillus* species.

It may also be desired to genetically engineer host cells of any type to produce a gram-positive metallo-protease. Such host cells are used in large scale fermentation to produce large quantities of the metallo-protease which may be isolated or purified and used in cleaning products, such as detergents.

I. Metallo-Protease Sequences

Gram positive polynucleotides having the nucleic acid sequence immediately downstream of the gram positive microorganism's major alkaline protease or subtilisn transcriptional terminator encode the gram positive MP. The *Bacillus subtilis* MP polynucleotides having the nucleic acid sequence immediately downstream from the putative transcriptional terminator of the aprE gene of *B. subtilis* I-168.

The nucleic acid sequence immediately downstream of the putative transcriptional terminator of aprE was subjected to nucleic acid sequencing and has the nucleic acid sequence and deduced amino acid sequence shown in FIGS. 1A-1E. As will be understood by the skilled artisan, due to the degeneracy of the genetic code, a variety of polynucleotides can encode the *Bacillus subtilis* MP. The present invention encompasses all such polynucleotides.

The present invention encompasses the use of MP polynucleotide homologs encoding gram-positive microorganism metallo-proteases MP which have at least 80%, or at least 90% or at least 95% identity to *B. subtilis* MP as long as the homolog encodes a protein that has proteolytic activity. A preferred MP polynucleotide homolog has 96% homology to *B. subtilis* MP.

Gram-positive polynucleotide homologs of *B. subtilis* MP may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y., Glover, D. M. (ed.), 1985, DNA Cloning: A Practical Approach, MRL Press, Ltd., Oxford, U.K. Vol. I, II.) A preferred source is from genomic DNA.

As will be understood by those of skill in the art, the polynucleotide sequence disclosed in FIGS. 1A-1E and amino acid sequences disclosed in FIGS. 3, 4 and 5, may reflect inadvertent errors inherent to nucleic acid sequencing technology. Nonetheless, one of ordinary skill in the art is fully capable of determining the correct sequences from the information provided herein regarding the invention. The present invention encompasses the naturally occurring nucleic acid molecule having the nucleic acid sequence obtained from the genomic sequence of *Bacillus* species.

Nucleic acid encoding *Bacillus subtilis* MP starts around 1102 kilobases counting from the point of origin in the *Bacillus subtilis* strain I-168 (Anagnostopala, 1961, J. Bacteriol. 81:741-746 or *Bacillus* Genomic Stock Center, accession 1A1, Columbus, Ohio). The *Bacillus subtilis* point of origin has been described in Ogasawara, N. (1995, Microbiology 141, Pt. 2 257-59) and Yoshikawa, H. (Nucleic Acids Research). *Bacillus subtilis* MP has a length of 426 amino acids. Based upon the location of the DNA encoding *Bacillus subtilis* MP and its proximity and relatedness to aprE, naturally occurring *B. subtilis* MP can be obtained by methods known to those of skill in the art including PCR technology.

Oligonucleotide sequences or primers of about 10-30 nucleotides in length can be designed from the polynucleotide sequence disclosed in FIGS. 1A-1E (SEQ ID NO:1) and used in PCR technology to isolate the naturally occurring sequence from *B. subtilis* genomic sequences.

Another general strategy for the "cloning" of *B. subtilis* genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic. DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned" DNA pieces. From the most external DNA sequence a new round of inverse PCR is started. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.).

Nucleic acid sequences derived from genomic DNA may contain regulatory regions in addition to coding regions. Whatever the source, the isolated MP gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the MP may be accomplished in a number of ways. For example, a *B. subtilis* MP gene of the present invention or its specific RNA, or a fragment thereof, such as a probe or primer, may be isolated and labeled and then used in hybridization assays to detect a gram-positive MP gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram-positive MP polynucleotide homologs which comprises hybridizing part or all of a nucleic acid sequence of *B. subtilis* MP with gram-positive microorganism nucleic acid of either genomic or cDNA origin.

Also included within the scope of the present invention is the use of gram-positive microorganism polynucleotide sequences that are capable of hybridizing to the nucleotide sequence of *B. subtilis* MP under conditions of intermediate to maximal stringency. Hybridization conditions are based on the melting temperature (Tm) of the nucleic acid binding complex, as taught in Berger and Kimmel (1987, *Guide to Molecular Cloning Techniques, Methods in Enzymology*, Vol 152, Academic Press, San Diego Calif.) incorporated herein by reference, and confer a defined "stringency" as explained below.

"Maximum stringency" typically occurs at about Tm–5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from *B. subtilis* MP preferably about 12 to 30 nucleotides, and more preferably about 20-25 nucleotides can be used as a probe or PCR primer.

The *B. subtilis* MP amino acid sequences (SEQ ID NO:2) shown in FIGS. 1A-1E were identified via a BLAST search (Altschul, Stephen, Basic local alignment search tool, J. Mol. Biol. 215:403-410) of *Bacillus subtilis* genomic nucleic acid sequences. *B. subtills* MP (YhfN) was identified by its overall nucleic acid identity to the metallo-protease, STE24 from *Saucharomyces cerevisiae* (SEQ ID NO:3), including the presence of the catalytic domain HEXXH +E as shown in FIGS. 2A-2B.

II. Expression Systems

The present invention provides host cells, expression methods and systems for the enhanced production and secretion of desired heterologous or homologous proteins in gram-positive microorganisms. In one embodiment, a host cell is genetically engineered to have a deletion or mutation in the gene encoding a gram-positive MP such that the respective activity is deleted. In another embodiment of the present invention, a gram-positive microorganism is genetically engineered to produce a metallo-protease of the present invention.

Inactivation of a Gram-positive Metallo-protease in a Host Cell

Producing an expression host cell incapable of producing the naturally occurring metallo-protease necessitates the replacement and/or inactivation of the naturally occurring gene from the genome of the host cell. In a preferred embodiment, the mutation is a non-reverting mutation.

One method for mutating nucleic acid encoding a gram-positive metallo-protease is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the metallo-protease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded metallo-protease gene. In another preferred embodiment, nucleic acid encoding the catalytic amino acid residues are deleted.

Deletion of the naturally occurring gram-positive microorganism metallo-protease can be carried out as follows. A metallo-protease gene including its 5' and 3' regions is isolated and inserted into a cloning vector. The coding region of the metallo-protease gene is deleted form the vector in vitro, leaving behind a sufficient amount of the 5' and 3' flanking sequences to provide for homologous recombination with the naturally occurring gene in the parent host cell. The vector is then transformed into the gram-positive host cell. The vector integrates into the chromosome via homologous recombination in the flanking regions. This method leads to a gram-positive strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the metallo-protease locus. Since illegitimate recombination will give different results it will be necessary to determine whether the complete gene has been deleted, such as through nucleic acid sequencing or restriction maps.

Another method of inactivating the naturally occurring metallo-protease gene is to mutagenize the chromosomal gene copy by transforming a gram-positive microorganism with oligonucleotides which are mutagenic. Alternatively, the chromosomal metallo-protease gene can be replaced with a mutant gene by homologous recombination.

The present invention encompasses host cells having additional protease deletions or mutations, such as deletions or mutations in apr, npr, epr, mpr and others known to those of skill in the art.

One assay for the detection of mutants involves growing the *Bacillus* host cell on medium containing a protease substrate and measuring the appearance or lack thereof, of a zone of clearing or halo around the colonies. Host cells which have an inactive protease will exhibit little or no halo around the colonies.

III. Production of Metallo-protease

For production of metallo-protease in a host cell, an expression vector comprising at least one copy of nucleic acid encoding a gram-positive microorganism MP, and preferably comprising multiple copies, is transformed into the host cell under conditions suitable for expression of the metallo-protease. In accordance with the present invention, polynucleotides which encode a gram-positive microorganism MP, or fragments thereof, or fusion proteins or polynucleotide homolog sequences that encode amino acid variants of *B. subtilis* MP, may be used to generate recombinant DNA molecules that direct their expression in host cells. In a preferred embodiment, the gram-positive host cell belongs to the genus *Bacillus*. In another preferred embodiment, the gram positive host cell is *B. subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477-508) can be selected, for example, to increase the rate of expression or to produce recombinant RNA transcripts having desirable properties, such as a longer half-life, than transcripts produced from naturally occurring sequence.

Altered MP polynucleotide sequences which may be used in accordance with the invention include deletions, insertions or substitutions of different nucleotide residues resulting in a polynucleotide that encodes the same or a functionally equivalent MP homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring MP.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent MP variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The MP polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a gram-positive microorganism MP polynucleotide may be ligated to a heterologous sequence to encode a fusion protein. A fusion protein may also be engineered to contain a cleavage site located between the metallo-protease nucleotide sequence and the heterologous protein sequence, so that the metallo-protease may be cleaved and purified away from the heterologous moiety.

IV. Vector Sequences

Expression vectors used in expressing the metallo-proteases of the present invention in gram-positive microorganisms comprise at least one promoter associated with a metallo-protease selected from the group consisting of MP, which promoter is functional in the host cell. In one embodiment of the present invention, the promoter is the wild-type promoter for the selected metallo-protease and in another embodiment of the present invention, the promoter is heterologous to the metallo-protease, but still functional in the host cell. In one preferred embodiment of the present invention, nucleic acid encoding the metallo-protease is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production *Bacillus subtilis* MP or MP homologs including bacterial, fungal, mammalian and insects cells. General transformation procedures are taught in Current Protocols In Molecular Biology (vol. 1, edited by Ausubel et al., John Wiley & Sons, Inc. 1987, Chapter 9) and include calcium phosphate methods, transformation using DEAE-Dextran and electroporation. Plant transformation methods are taught in Rodriquez (WO 95/14099, published 26 May 1995).

In a preferred embodiment, the host cell is a gram-positive microorganism and in another preferred embodiment, the host cell is *Bacillus*. In one embodiment of the present invention, nucleic acid encoding one or more metalloprotease(s) of the present invention is introduced into a host cell via an expression vector capable of replicating within the *Bacillus* host cell. Suitable replicating plasmids for *Bacillus* are described in Molecular Biological Methods for *Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a metalloprotease(s) of the present invention is stably integrated into the microorganism genome. Preferred host cells are gram-positive host cells. Another preferred host is *Bacillus*. Another preferred host is *Bacillus subtilis*. Several strategies have been described in the literature for the direct cloning of DNA in *Bacillus*. Plasmid marker rescue transformation involves the uptake of a donor plasmid by competent cells carrying a partially homologous resident plasmid (Contente et al., Plasmid 2:555-571 (1979); Haima et al., Mol. Gen. Genet. 223:185-191 (1990); Weinrauch et al., J. Bacteriol. 154(3):1077-1087 (1983); and Weinrauch et al., J. Bacteriol. 169(3):1205-1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111-115; for *B. megaterium* in Vorobjeva et al., (1980) FEMS Microbiol. Letters 7:261-263; for *B. amyloliquefaciens* in Smith et al., (1986) Appl. and Env. Microbiol. 51:634; for *B. thuringiensis* in Fisher et al., (1981) Arch. Microbiol. 139:213-217; for *B. sphaericus* in McDonald (1984) J. Gen. Microbiol. 130:203; and *B. larvae* in Bakhiet et al., (I985, Appl. Environ. Microbiol. 49:577). Mann et al., (1986, Current Microbiol. 13:131-135) report on transformation of *Bacillus* protoplasts and Holubova, (1985) Folia Microbiol. 30:97) disclose methods for introducing DNA into protoplasts using DNA containing liposomes.

VI. Identification of Transformants

Whether a host cell has been transformed with a mutated or a naturally occurring gene encoding a gram-positive MP, detection of the presence/absence of marker gene expression can suggest whether the gene of interest is present. However, its expression should be confirmed. For example, if the nucleic acid encoding a metallo-protease is inserted within a marker gene sequence, recombinant cells containing the insert can be identified by the absence of marker gene function. Alternatively, a marker gene can be placed in tandem with nucleic acid encoding the metallo-protease under the control of a single promoter. Expression of the marker gene in response to induction or selection usually indicates expression of the metallo-protease as well.

Alternatively, host cells which contain the coding sequence for a metallo-protease and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the metallo-protease polynucleotide sequence can be detected by DNA-DNA or DNA-RNA hybridization or amplification using probes, portions or fragments of *B. subtilis* MP.

VII. Assay of Protease Activity

There are various assays known to those of skill in the art for detecting and measuring protease activity. There are assays based upon the release of acid-soluble peptides from casein or hemoglobin measured as absorbance at 280 nm or colorimetrically using the Folin method (Bergmeyer, et al., 1984, Methods of Enzymatic Analysis vol. 5, Peptidases, Proteinases and their Inhibitors, Verlag Chemie, Weinheim). Other assays involve the solubilization of chromogenic substrates (Ward, 1983, Proteinases, in Microbial Enzymes and Biotechnology (W. M. Fogarty, ed.), Applied Science, London, pp. 251-317).

VIII. Secretion of Recombinant Proteins

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a mutation or deletion of the metallo-protease activity will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441-53).

Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of the Present Invention

MP and Genetically Engineered Host Cells

The present invention provides genetically engineered host cells comprising mutations, preferably non-revertable mutations, or deletions in the naturally occurring gene encoding MP such that the proteolytic activity is diminished or deleted altogether. The host cell may contain additional protease deletions, such as deletions of the mature subtilisn protease and/or mature neutral protease disclosed in U.S. Pat. No. 5,264,366.

In a preferred embodiment, the host cell is further genetically engineered to produce a desired protein or polypeptide. In a preferred embodiment the host cell is a *Bacillus*. In another preferred embodiment, the host cell is a *Bacillus subtilis*.

In an alternative embodiment, a host cell is genetically engineered to produce a gram-positive MP. In a preferred embodiment, the host cell is grown under large scale fermentation conditions. In another preferred embodiment, the MP is isolated and/or purified and used in the textile industry, the feed industry and in cleaning compositions such as detergents.

As noted, MP can be useful in formulating various cleaning compositions. A number of known compounds are suitable surfactants useful in compositions comprising the MP of the invention. These include nonionic, anionic, cationic, anionic or zwitterionic detergents, as disclosed in U.S. Pat. No. 4,404,128 and U.S. Pat. No. 4,261,868. A suitable detergent formulation is that described in Example 7 of U.S. Pat. No. 5,204,015. The art is familiar with the different formulations which can be used as cleaning compositions. In addition, MP can be used, for example, in bar or liquid soap applications, dishcare formulations, contact lens cleaning solutions or products, peptide hydrolysis, waste treatment, textile applications, as fusion-cleavage enzymes in protein production, etc. MP may comprise enhanced performance in a detergent composition (as compared to another detergent protease). As used herein, enhanced performance in a detergent is defined as increasing cleaning of certain enzyme sensitive stains such as grass or blood, as determined by usual evaluation after a standard wash cycle.

MP can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of MP to conventional cleaning compositions does not create any special use limitation. In other words, any temperature and pH suitable for the detergent is also suitable for the present compositions as long as the pH is within the above range, and the temperature is below the described MP's denaturing temperature. In addition, MP can be used in a cleaning composition without detergents, again either alone or in combination with builders and stabilizers.

Proteases can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes MP. The composition can be used to treat for example silk or wool as described in publications such as RD 216,034; EP 134,267; U.S. Pat. No. 4,533,359; and EP 344,259.

MP Polynucleotides

A *B. subtilis* MP polynucleotide, or any part thereof, provides the basis for detecting the presence of gram-positive microorganism MP polynucleotide homologs through hybridization techniques and PCR technology.

Accordingly, one aspect of the present invention is to provide for nucleic acid hybridization and PCR probes which can be used to detect polynucleotide sequences, including genomic and cDNA sequences, encoding gram-positive MP or portions thereof. In another aspect of the present invention, an MP polynucleotide can be used in hybridization technology to detect the major protease of a gram-positive microorganism due to the proximity of the MP with the major protease.

The manner and method of carrying out the present invention may be more fully understood by those of skill in the art by reference to the following examples, which examples are not intended in any manner to limit the scope of the present invention or of the claims directed thereto.

EXAMPLE I

Preparation of a Genomic Library

The following example illustrates the preparation of a *Bacillus* genomic library.

Genomic DNA from *Bacillus* cells is prepared as taught in Current Protocols In Molecular Biology vol. 1, edited by Ausubel et al., John Wiley & Sons, Inc. 1987, chapter 2. 4.1. Generally, *Bacillus* cells from a saturated liquid culture are lysed and the proteins removed by digestion with proteinase K. Cell wall debris, polysaccharides, and remaining proteins are removed by selective precipitation with CTAB, and high molecular weight genomic DNA is recovered from the resulting supernatant by isopropanol precipitation. If exceptionally clean genomic DNA is desired, an additional step of purifying the *Bacillus* genomic DNA on a cesium chloride gradient is added.

After obtaining purified genomic DNA, the DNA is subjected to Sau3A digestion. Sau3A recognizes the 4 base pair site GATC and generates fragments compatible with several convenient phage lambda and cosmid vectors. The DNA is subjected to partial digestion to increase the chance of obtaining random fragments.

The partially digested *Bacillus* genomic DNA is subjected to size fractionation on a 1% agarose gel prior to cloning into a vector. Alternatively, size fractionation on a sucrose gradient can be used. The genomic DNA obtained from the size fractionation step is purified away from the agarose and ligated into a cloning vector appropriate for use in a host cell and transformed into the host cell.

EXAMPLE II

Detection of Gram-positive Microorganisms

The following example describes the detection of gram-positive microorganism MP.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from MP.

The nucleic acid probe is labeled by combining 50 pmol of the nucleic acid and 250 mCi of [gamma $^{32}$P] adenosine triphosphate (Amersham, Chicago Ill.) and T4 polynucleotide kinase (DuPont NEN®, Boston Mass.). The labeled probe is purified with Sephadex G-25 super fine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1× saline sodium citrate and 0.5% sodium dodecyl sulfate.

The blots are exposed to film for several hours, the film developed and hybridization patterns are compared visually to detect polynucleotide homologs of *B. subtilis* MP. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

I claim:

1. A method for detecting a polynucleotide encoding a gram-positive microorganism metalloprotease comprising the steps of:

(a) hybridizing a gram-positive microorganism polynucleotide to a probe that comprises the nucleic acid sequence of SEQ ID NO:1 from position 326 through position 1603;

(b) isolating said gram-positive polynucleotide which hybridizes to said probe; and (c) verifying that said polynucleotide which hybridizes to said probe comprises a polynucleotide sequence that encodes a metalloprotease.

2. The method of claim 1, wherein said gram-positive microorganism is a species of the genus *Bacillus*.

3. The method of claim 2, wherein said *Bacillus* species is selected from the group consisting of *B. subtilis, B. licheniformis, B. lentus, B. brevis, B. stearothermophilus, B. alkalophilus, B. amyloliquefaciens, B. coagulans, B. circulans, B. lautus,* and *B. thuringiensis*.

* * * * *

SEQUENCE LISTING

<160> NUMBER OF SEQ ID NOS: 6

<210> SEQ ID NO 1
<211> LENGTH: 2760
<212> TYPE: DNA
<213> ORGANISM: Bacillus subtilis

<400> SEQUENCE: 1

```
cagcatatct ttgacgtgct gtcttttttc aatctcgata tcttcctggc cgcttgaaga      60
cagtgtgatc aaatccgcgt ctaccgattg atacacatcg cctgatcggc tgtaaagata     120
aaaaaatgcg ataaacacaa gaccgattac cacgatggct gccactattt ttttcatttg     180
catcactcca aacattgtta gttttcccag cgatcggggt ttccatgctt aaaagggtgg     240
aaaagtgcgg aacacagctt ggttctaaga atttgaattt atgattacaa tagaagtaac     300
gggttgatgt gaggagtgag gcgttatgcg caagtggatt gcggcagcag gacttgctta     360
cgtgctgtac gggctgtttt tttattggta ttttttcctg tcgggtgatt ccgcaatacc     420
ggaagccgtg aaagggacgc aggctgatcc ggcttctttc atgaagccgt ctgagttggc     480
agtggccgag cagtattcga atgtcaagaa tttttttattt tttatcgggg taccacttga     540
ttggtttctg tttttttgttc tgcttgtcag cggtgtttca aagaaaatca agaaatggat     600
cgaagcggcc gtgccttttc ggttttttgca gaccgttggt tttgtgtttg tgctttcgct     660
gattacaaca ttggtgacgc tgcctttaga ttggataggc tatcaagtat cgcttgacta     720
taacatttcc acacagacaa cggccagctg ggctaaggat caggttatca gcttttggat     780
cagctttcca atctttacgc tttgcgttct cgttttttat tggctgatca aaaggcatga     840
aaaaaaatgg tggttatacg cctggctgtt aacagtgccg ttttcgctgt ttctgttttt     900
tattcagccg gtcattatcg atcctttata caatgatttt tatccgctga aaaacaaaga     960
gcttgaaagc aaaatttttag agctggcaga tgaagccaat attccggctg accatgtata    1020
tgaagtgaac atgtcagaaa aaacaaatgc gctgaatgcc tatgttacag gaattggggc    1080
caataaacgg attgtattgt gggatacgac gctgaacaaa cttgacgatt cagaaattct    1140
gtttattatg ggccacgaaa tgggccatta tgtcatgaag cacgtttaca tcggtctggc    1200
tggctatttg ctcgtgtcgc tcgccggatt ttatgtcatt gataagcttt acaagcggac    1260
```

-continued

```
ggttcgccta acccgcagca tgtttcattt agaagggcgg catgatcttg cggcacttcc    1320
gctgttattg cttttgtttt ctgttttgag ctttgcggtt acgccttttt ctaatgctgt    1380
ctcgcgttat caggagaata aggctgacca gtatgggatc gagttgacag agaacagaga    1440
agccgctgtt aaaacgtttc aggatttggc cgtgacgggg ctgagccagg ttgatcctcc    1500
ggtgcttgtg aagattttca gaggcagcca tccgtcgatc atggaacgga ttcaacatgc    1560
ggagaaagaa gagaatgcgc cggaacatca ggatgctgac aaataaaaag aagcaggtat    1620
ggaggaacct gcttcttttt actattattg tgcagctgct tgtacgttga ttaaccctt     1680
tccatagtag aaagagtttc caagatatgt tgcagtgctt tctaaacgat cacggacttg    1740
cgcgtttgtc caagtcgggt gcttagaaag aattaacgct gctgctccgg caacgtgagg    1800
agtcgccatg gacgttccgt tataagcgcc gtaagtgcct ccaggaagtg tgctttggat    1860
ggacacgcca ggagccatca catcaagctc agaacctgcg ctggagaatg aagctctttg    1920
gttgctgctg tttaccgcac ctactgcaat agtagaagga tattttgcag ggtagccgac    1980
tgtgcttgtg cttccggatg aaccttcgtt tccggctgcg gcagcaacga cgataccgct    2040
ggaaacggct ttgtcaacga ctgttttcag cgctgtagaa ccagtaggtc cgccaaggct    2100
catgttgata acatccatat tgttggaaat ggcccactca atgccgttaa taatccagct    2160
atattgccg cttcctgttg aatcaagcac ttttactgca tataatgatg cgcttgggct     2220
aacgcccaga caccgattg agttattaag agcggcaatc gtaccggcta catgcgtacc     2280
gtgagaactg ccgtcctggt atgggtttgt ttcagaaggt acgaagcttg ctccgcctct    2340
gacgtttaag tcaggatgag aagagtcaat tccgctgtcg ataacagcta cttttacgtt    2400
agagcctgtg tagccttgag agtgaagagc cggcgcttta atttgagaaa tgccataagg    2460
aacagattgc gcatattcat gtgcaatatg atcttcttcc acatatgcaa cgctcggatc    2520
ttttttcaat tcttttacag ctttttcatc caatgttgct gcggccgcgt taacatactt    2580
aaattgcttt tgaacctttc cgcctttttc agaaataaca tccttttttct tggcggaact   2640
catggcactc attgtctgtt taaatccgac aatgtatttc ttttctgtac tgctttttcc    2700
ggcagcctgc acagacatgt tgctgaacgc catcgtaaag attaacgtta acgcaaacaa    2760
```

<210> SEQ ID NO 2
<211> LENGTH: 426
<212> TYPE: PRT
<213> ORGANISM: Bacillus subtilis

<400> SEQUENCE: 2

```
Met Arg Lys Trp Ile Ala Ala Gly Leu Ala Tyr Val Leu Tyr Gly
  1               5                  10                  15

Leu Phe Phe Tyr Trp Tyr Phe Phe Leu Ser Gly Asp Ser Ala Ile Pro
                 20                  25                  30

Glu Ala Val Lys Gly Thr Gln Ala Asp Pro Ala Ser Phe Met Lys Pro
             35                  40                  45

Ser Glu Leu Ala Val Ala Glu Gln Tyr Ser Asn Val Lys Asn Phe Leu
         50                  55                  60

Phe Phe Ile Gly Val Pro Leu Asp Trp Phe Phe Val Leu Leu
 65                  70                  75                  80

Val Ser Gly Val Ser Lys Lys Ile Lys Lys Trp Ile Glu Ala Ala Val
                 85                  90                  95

Pro Phe Arg Phe Leu Gln Thr Val Gly Phe Val Phe Val Leu Ser Leu
                100                 105                 110
```

Ile Thr Thr Leu Val Thr Leu Pro Leu Asp Trp Ile Gly Tyr Gln Val
            115                 120                 125

Ser Leu Asp Tyr Asn Ile Ser Thr Gln Thr Thr Ala Ser Trp Ala Lys
        130                 135                 140

Asp Gln Val Ile Ser Phe Trp Ile Ser Phe Pro Ile Phe Thr Leu Cys
145                 150                 155                 160

Val Leu Val Phe Tyr Trp Leu Ile Lys Arg His Glu Lys Lys Trp Trp
                165                 170                 175

Leu Tyr Ala Trp Leu Leu Thr Val Pro Phe Ser Leu Phe Leu Phe Phe
            180                 185                 190

Ile Gln Pro Val Ile Ile Asp Pro Leu Tyr Asn Asp Phe Tyr Pro Leu
        195                 200                 205

Lys Asn Lys Glu Leu Glu Ser Lys Ile Leu Glu Leu Ala Asp Glu Ala
210                 215                 220

Asn Ile Pro Ala Asp His Val Tyr Glu Val Asn Met Ser Glu Lys Thr
225                 230                 235                 240

Asn Ala Leu Asn Ala Tyr Val Thr Gly Ile Gly Ala Asn Lys Arg Ile
                245                 250                 255

Val Leu Trp Asp Thr Thr Leu Asn Lys Leu Asp Asp Ser Glu Ile Leu
            260                 265                 270

Phe Ile Met Gly His Glu Met Gly His Tyr Val Met Lys His Val Tyr
        275                 280                 285

Ile Gly Leu Ala Gly Tyr Leu Leu Val Ser Leu Ala Gly Phe Tyr Val
        290                 295                 300

Ile Asp Lys Leu Tyr Lys Arg Thr Val Arg Leu Thr Arg Ser Met Phe
305                 310                 315                 320

His Leu Glu Gly Arg His Asp Leu Ala Ala Leu Pro Leu Leu Leu Leu
                325                 330                 335

Leu Phe Ser Val Leu Ser Phe Ala Val Thr Pro Phe Ser Asn Ala Val
            340                 345                 350

Ser Arg Tyr Gln Glu Asn Lys Ala Asp Gln Tyr Gly Ile Glu Leu Thr
        355                 360                 365

Glu Asn Arg Glu Ala Ala Val Lys Thr Phe Gln Asp Leu Ala Val Thr
        370                 375                 380

Gly Leu Ser Gln Val Asp Pro Val Leu Val Lys Ile Phe Arg Gly
385                 390                 395                 400

Ser His Pro Ser Ile Met Glu Arg Ile Gln His Ala Glu Lys Glu Glu
                405                 410                 415

Asn Ala Pro Glu His Gln Asp Ala Asp Lys
            420                 425

<210> SEQ ID NO 3
<211> LENGTH: 472
<212> TYPE: PRT
<213> ORGANISM: S. cerevisiae

<400> SEQUENCE: 3

Met Phe Asp Leu Lys Thr Ile Leu Asp His Pro Asn Ile Pro Trp Lys
1               5                   10                  15

Leu Ile Ile Ser Gly Phe Ser Ile Ala Gln Phe Ser Phe Glu Ser Tyr
            20                  25                  30

Leu Thr Tyr Arg Gln Tyr Gln Lys Leu Ser Glu Thr Lys Leu Pro Pro
        35                  40                  45

Val Leu Glu Asp Glu Ile Asp Asp Glu Thr Phe His Lys Ser Arg Asn
    50                  55                  60

-continued

```
Tyr Ser Arg Ala Lys Ala Lys Phe Ser Ile Phe Gly Asp Val Tyr Asn
 65                  70                  75                  80

Leu Ala Gln Lys Leu Val Phe Ile Lys Tyr Asp Leu Phe Pro Lys Ile
             85                  90                  95

Trp His Met Ala Val Ser Leu Leu Asn Ala Val Leu Pro Val Arg Phe
            100                 105                 110

His Met Val Ser Thr Val Ala Gln Ser Leu Cys Phe Leu Gly Leu Leu
            115                 120                 125

Ser Ser Leu Ser Thr Leu Val Asp Leu Pro Leu Ser Tyr Tyr Ser His
    130                 135                 140

Phe Val Leu Glu Glu Lys Phe Gly Phe Asn Lys Leu Thr Val Gln Leu
145                 150                 155                 160

Trp Ile Thr Asp Met Ile Lys Ser Leu Thr Leu Ala Tyr Ala Ile Gly
                165                 170                 175

Gly Pro Ile Leu Tyr Leu Phe Leu Lys Ile Phe Asp Lys Phe Pro Thr
                180                 185                 190

Asp Phe Leu Trp Tyr Ile Met Val Phe Leu Phe Val Val Gln Ile Leu
            195                 200                 205

Ala Met Thr Ile Ile Pro Val Phe Ile Met Pro Met Phe Asn Lys Phe
    210                 215                 220

Thr Pro Leu Glu Asp Gly Glu Leu Lys Lys Ser Ile Glu Ser Leu Ala
225                 230                 235                 240

Asp Arg Val Gly Phe Pro Leu Asp Lys Ile Phe Val Ile Asp Gly Ser
                245                 250                 255

Lys Arg Ser Ser His Ser Asn Ala Tyr Phe Thr Gly Leu Pro Phe Thr
            260                 265                 270

Ser Lys Arg Ile Val Leu Phe Asp Thr Leu Val Asn Ser Asn Ser Thr
    275                 280                 285

Asp Glu Ile Thr Ala Val Leu Ala His Glu Ile Gly His Trp Gln Lys
290                 295                 300

Asn His Ile Val Asn Met Val Ile Phe Ser Gln Leu His Thr Phe Leu
305                 310                 315                 320

Ile Phe Ser Leu Phe Thr Ser Ile Tyr Arg Asn Thr Ser Phe Tyr Asn
                325                 330                 335

Thr Phe Gly Phe Phe Leu Glu Lys Ser Thr Gly Ser Phe Val Asp Pro
            340                 345                 350

Val Ile Thr Lys Glu Phe Pro Ile Ile Gly Phe Met Leu Phe Asn
    355                 360                 365

Asp Leu Leu Thr Pro Leu Glu Cys Ala Met Gln Phe Val Met Ser Leu
370                 375                 380

Ile Ser Arg Thr His Glu Tyr Gln Ala Asp Ala Tyr Ala Lys Lys Leu
385                 390                 395                 400

Gly Tyr Lys Gln Asn Leu Cys Arg Ala Leu Ile Asp Leu Gln Ile Lys
                405                 410                 415

Asn Leu Ser Thr Met Asn Val Asp Pro Leu Tyr Ser Ser Tyr His Tyr
            420                 425                 430

Ser His Pro Thr Leu Ala Glu Arg Leu Thr Ala Leu Asp Tyr Val Ser
    435                 440                 445

Glu Lys Lys Lys Asn Thr His Glu Ala Asx Val Glu Arg Glu Pro Arg
    450                 455                 460

Thr Ile Asn Phe Arg Met Ala Thr
465                 470
```

```
<210> SEQ ID NO 4
<211> LENGTH: 474
<212> TYPE: PRT
<213> ORGANISM: Schizocaccharomyces pombe

<400> SEQUENCE: 4
```

| | | | | | | | | | | | | | | | |
|---|---|---|---|---|---|---|---|---|---|---|---|---|---|---|---|
| Met | Ser | Pro | Gly | Leu | Cys | Phe | Leu | Lys | Glu | Ile | Ser | Val | Ile | Gln | Ala |
| 1 | | | | 5 | | | | | 10 | | | | | 15 | |
| Thr | Pro | Lys | Pro | Thr | Thr | Arg | Ser | Phe | Ala | Asn | Cys | Cys | Lys | Met | Gly |
| | | | 20 | | | | | 25 | | | | | 30 | | |
| Ile | Leu | Gln | His | Leu | Met | His | Ile | Leu | Asp | Ile | Pro | Gly | Phe | Pro | Trp |
| | | | 35 | | | | 40 | | | | | 45 | | | |
| Lys | Ile | Val | Ile | Ala | Gly | Phe | Ser | Ile | Gly | Lys | Tyr | Ala | Trp | Asp | Leu |
| | 50 | | | | | 55 | | | | | 60 | | | | |
| Tyr | Leu | Arg | Arg | Arg | Gln | Val | Pro | Tyr | Leu | Leu | Arg | Glu | Lys | Pro | Pro |
| 65 | | | | | 70 | | | | | 75 | | | | | 80 |
| Ala | Ile | Leu | Ala | Glu | His | Val | Asp | Glu | Lys | Lys | Tyr | Gln | Lys | Ala | Leu |
| | | | | 85 | | | | | 90 | | | | | 95 | |
| Ser | Tyr | Ala | Arg | Asp | Lys | Ser | Trp | Phe | Ser | Thr | Ile | Val | Ser | Thr | Phe |
| | | | 100 | | | | | 105 | | | | | 110 | | |
| Thr | Leu | Ala | Val | Asp | Leu | Leu | Ile | Ile | Lys | Tyr | Asp | Gly | Leu | Ser | Tyr |
| | | | 115 | | | | | 120 | | | | | 125 | | |
| Leu | Trp | Asn | Ile | Thr | Lys | Phe | Pro | Trp | Met | Asp | Lys | Leu | Ala | Ala | Ser |
| | 130 | | | | | 135 | | | | | 140 | | | | |
| Ser | Ser | Arg | Phe | Ser | Leu | Ser | Thr | Ser | Ile | Thr | His | Ser | Cys | Val | Phe |
| 145 | | | | | 150 | | | | | 155 | | | | | 160 |
| Met | Phe | Gly | Leu | Thr | Leu | Phe | Ser | Arg | Leu | Ile | Gln | Ile | Pro | Phe | Asn |
| | | | | 165 | | | | | 170 | | | | | 175 | |
| Leu | Tyr | Ser | Thr | Phe | Val | Ile | Glu | Glu | Lys | Tyr | Gly | Phe | Asn | Lys | Ser |
| | | | 180 | | | | | 185 | | | | | 190 | | |
| Thr | Leu | Lys | Ile | Phe | Val | Ile | Asp | Leu | Leu | Lys | Glu | Leu | Ser | Leu | Gly |
| | | | 195 | | | | | 200 | | | | | 205 | | |
| Gly | Leu | Leu | Met | Ser | Val | Val | Gly | Val | Phe | Val | Lys | Ile | Leu | Thr | |
| | 210 | | | | | 215 | | | | | 220 | | | | |
| Lys | Phe | Gly | Asp | Asn | Phe | Ile | Met | Tyr | Ala | Trp | Gly | Ala | Tyr | Ile | Val |
| 225 | | | | | 230 | | | | | 235 | | | | | 240 |
| Phe | Gly | Leu | Ile | Leu | Gln | Thr | Ile | Ala | Pro | Ser | Leu | Ile | Met | Pro | Leu |
| | | | | 245 | | | | | 250 | | | | | 255 | |
| Phe | Tyr | Lys | Phe | Thr | Pro | Leu | Glu | Asn | Gly | Ser | Leu | Arg | Thr | Gln | Ile |
| | | | 260 | | | | | 265 | | | | | 270 | | |
| Glu | Glu | Leu | Ala | Ala | Ser | Ile | Asn | Phe | Pro | Leu | Lys | Lys | Leu | Tyr | Val |
| | | | 275 | | | | | 280 | | | | | 285 | | |
| Ile | Asp | Ala | Ser | Arg | Arg | Ser | Thr | His | Ser | Asn | Ala | Phe | Phe | Tyr | Gly |
| | 290 | | | | | 295 | | | | | 300 | | | | |
| Leu | Pro | Trp | Asn | Lys | Gly | Ile | Val | Leu | Phe | Asp | Thr | Leu | Val | Lys | Asn |
| 305 | | | | | 310 | | | | | 315 | | | | | 320 |
| His | Thr | Glu | Pro | Glu | Leu | Ile | Ala | Ile | Leu | Gly | His | Glu | Leu | Gly | His |
| | | | | 325 | | | | | 330 | | | | | 335 | |
| Trp | Tyr | Met | Ser | His | Asn | Leu | Ile | Asn | Thr | Ile | Asp | Tyr | Gly | Met | |
| | | | 340 | | | | | 345 | | | | | 350 | | |
| Ser | Leu | Phe | His | Leu | Phe | Leu | Phe | Ala | Ala | Phe | Ile | Arg | Asn | Asn | Ser |
| | | | 355 | | | | | 360 | | | | | 365 | | |
| Leu | Tyr | Thr | Ser | Phe | Asn | Phe | Ile | Thr | Glu | Lys | Pro | Val | Ile | Val | Gly |
| | 370 | | | | | 375 | | | | | 380 | | | | |

-continued

```
Leu Leu Leu Phe Ser Asp Ala Leu Gly Pro Leu Ser Ser Ile Leu Thr
385                 390                 395                 400

Phe Ala Ser Asn Lys Val Ser Arg Leu Cys Glu Tyr Gln Ala Asp Ala
            405                 410                 415

Phe Ala Lys Gln Leu Gly Tyr Ala Lys Asp Leu Gly Asp Gly Leu Ile
            420                 425                 430

Arg Ile His Asp Asp Asn Leu Ser Pro Leu Glu Phe Asp Ser Leu Tyr
            435                 440                 445

Thr Ser Tyr Tyr His Ser His Pro Ile Leu Val Asp Arg Leu Asn Ala
            450                 455                 460

Ile Asp Tyr Thr Thr Leu Lys Lys Asn Asn
465                 470

<210> SEQ ID NO 5
<211> LENGTH: 215
<212> TYPE: PRT
<213> ORGANISM: E. coli

<400> SEQUENCE: 5

Met Met Arg Ile Ala Leu Phe Leu Leu Thr Asn Leu Ala Val Met Val
1               5                   10                  15

Val Phe Gly Leu Val Leu Ser Leu Thr Gly Ile Gln Ser Ser Ser Val
            20                  25                  30

Gln Gly Leu Met Ile Met Ala Leu Leu Phe Gly Phe Gly Gly Ser Phe
        35                  40                  45

Val Ser Leu Leu Met Ser Lys Trp Met Ala Leu Arg Ser Val Gly Gly
    50                  55                  60

Glu Val Ile Glu Gln Pro Arg Asn Glu Arg Glu Arg Trp Leu Val Asn
65                  70                  75                  80

Thr Val Ala Thr Gln Ala Arg Gln Ala Gly Ile Ala Met Pro Gln Val
                85                  90                  95

Ala Ile Tyr His Ala Pro Asp Ile Asn Ala Phe Ala Thr Gly Ala Arg
            100                 105                 110

Arg Asp Ala Ser Leu Val Ala Val Ser Thr Gly Leu Leu Gln Asn Met
            115                 120                 125

Ser Pro Asp Glu Ala Glu Ala Val Ile Ala His Glu Ile Ser His Ile
        130                 135                 140

Ala Asn Gly Asp Met Val Thr Met Thr Leu Ile Gln Gly Val Val Asn
145                 150                 155                 160

Thr Phe Val Ile Phe Ile Ser Arg Ile Leu Ala Gln Leu Ala Ala Gly
                165                 170                 175

Phe Met Gly Gly Asn Arg Asp Glu Gly Glu Ser Asn Gly Asn Pro
            180                 185                 190

Leu Ile Tyr Phe Ala Val Ala Thr Val Leu Glu Leu Val Phe Gly Ile
        195                 200                 205

Leu Ala Ser Ile Ile Thr Met
    210                 215

<210> SEQ ID NO 6
<211> LENGTH: 283
<212> TYPE: PRT
<213> ORGANISM: Haemophilis influenza

<400> SEQUENCE: 6

Met Met Arg Ile Leu Leu Phe Leu Ala Thr Asn Met Ala Val Met Leu
1               5                   10                  15
```

```
Val Leu Gly Ile Ile Leu Ser Val Thr Gly Ile Ala Gly Asn Ser Thr
            20                  25                  30

Gly Gly Ile Leu Ile Met Ala Leu Leu Phe Gly Phe Ala Gly Ser Leu
            35                  40                  45

Ile Ser Leu Phe Leu Ser Lys Thr Met Ala Leu Arg Ser Val Asp Gly
    50                  55                  60

Glu Val Ile Thr Gln Pro Arg Asn Gln Thr Glu Arg Trp Leu Ile Asp
65                      70                  75                  80

Thr Val Ser Arg Gln Ala Gln Lys Ala Gly Ile Pro Met Pro Asp Val
                85                  90                  95

Ala Ile Tyr His Ser Pro Asp Val Asn Ala Phe Ala Thr Gly Ala Thr
                100                 105                 110

Lys Ser Asn Ser Leu Val Ala Val Ser Thr Gly Leu Leu Asn Asn Met
                115                 120                 125

Thr Glu Ala Glu Ala Glu Ala Val Leu Ala His Glu Ile Ser His Ile
    130                 135                 140

Ser Asn Gly Asp Met Val Thr Met Ala Leu Leu Gln Gly Val Leu Asn
145                     150                 155                 160

Thr Phe Val Ile Phe Leu Ser Arg Val Ile Ala Thr Ala Val Ala Ser
                165                 170                 175

Ser Arg Asn Asn Asn Gly Glu Glu Thr Arg Ser Ser Gly Ile Tyr Phe
            180                 185                 190

Leu Val Ser Met Val Leu Glu Met Leu Phe Gly Val Leu Ala Ser Ile
                195                 200                 205

Ile Ala Met Trp Phe Ser Arg Tyr Arg Glu Phe Arg Ala Asp Ala Gly
    210                 215                 220

Ser Ala Ser Leu Val Gly Lys Glu Lys Met Ile Met Ala Leu Gln Arg
225                 230                 235                 240

Leu Gln Gln Leu His Glu Pro Gln Asn Leu Glu Gly Ser Leu Asn Ala
                245                 250                 255

Phe Met Ile Asn Gly Lys Arg Ser Glu Leu Phe Met Ser His Pro Pro
            260                 265                 270

Leu Glu Lys Arg Ile Glu Ala Leu Arg Asn Leu
            275                 280
```